(12) United States Patent
Moseley

(10) Patent No.: US 6,660,231 B2
(45) Date of Patent: Dec. 9, 2003

(54) SENSORS FOR OXIDIZING GASES

(75) Inventor: Patrick T. Moseley, Chapel Hill, NC (US)

(73) Assignee: Atmospheric Sensors, LLC, King of Prussia, PA (US)

( * ) Notice: Subject to any disclaimer, the term of this patent is extended or adjusted under 35 U.S.C. 154(b) by 314 days.

(21) Appl. No.: 09/833,605

(22) Filed: Apr. 13, 2001

(65) Prior Publication Data

US 2001/0035042 A1 Nov. 1, 2001

Related U.S. Application Data

(60) Provisional application No. 60/196,918, filed on Apr. 13, 2000.

(51) Int. Cl.[7] .......................... G01N 27/00; G01N 21/00; G01N 30/96; G01N 9/00; G01N 33/497
(52) U.S. Cl. .............................. 422/98; 422/83; 422/88; 73/1.01; 73/1.02; 73/23.2; 73/23.31; 436/106; 436/116; 436/127; 436/149
(58) Field of Search .................................. 436/116, 149, 436/106, 127; 422/50, 83, 98, 88; 73/1.01, 1.02, 23.2, 23.31

(56) References Cited

U.S. PATENT DOCUMENTS

| | | | |
|---|---|---|---|
| 4,045,178 A | * | 8/1977 | Okinaka et al. ............... 422/98 |
| 4,067,695 A | * | 1/1978 | Miyaguchi ................... 422/98 |
| 4,307,373 A | | 12/1981 | Johnston |
| 4,314,996 A | | 2/1982 | Sekido et al. |
| 4,335,369 A | | 6/1982 | Taniguchi et al. |
| 4,454,494 A | | 6/1984 | Williams et al. |
| 4,469,626 A | | 9/1984 | Tuohig et al. |
| 4,574,264 A | | 3/1986 | Takahashi et al. |
| 4,677,414 A | | 6/1987 | Yates |
| 4,720,993 A | | 1/1988 | Badwal |
| 5,071,626 A | | 12/1991 | Tuller |
| 5,397,541 A | | 3/1995 | Post |
| 5,792,666 A | | 8/1998 | Härdtl et al. |
| 5,811,662 A | | 9/1998 | Williams et al. |
| 5,843,858 A | | 12/1998 | Hardtl et al. |
| 5,876,673 A | | 3/1999 | Logothetis et al. |
| 5,972,296 A | | 10/1999 | Hardtl et al. |
| 6,548,024 B1 | * | 4/2003 | Doncaster et al. ............ 422/88 |

* cited by examiner

Primary Examiner—Jill Warden
Assistant Examiner—Brian Sines
(74) Attorney, Agent, or Firm—James Creighton Wray; Meera P. Narasimhan

(57) ABSTRACT

The mixed oxide $W_xMo_{1-x}O_3$, where preferably x can be in the range 0.01 to 0.9, is very useful for the detection of oxidizing gases and in particular is superior for the detection of ozone. The preferred composition is in the range of 1% to 21% Mo (i.e. 99% to 79% W). The present example in which the composition of the sensing material is in the range $W_xMo_{1-x}O_3$ with x varying from 0.01 to 0.9, is clearly distinct from the device claimed in applicant's earlier patent. Precipitation of the material as a mixed oxide from an aqueous solution of the ammonium metallates in concentrations of the appropriate stoichiometric proportions yields a powder that can be screen-printed to give an ideal microstructure. Resistivity of the material may be tailored to a desired value by adjusting the Mo/W ratio within the single phase field. Varying this ratio adjusts catalytic properties of the material.

18 Claims, 2 Drawing Sheets

SENSORS FOR OXIDIZING GASES

This application claims the benefit of U.S. Provisional Application No. 60/196,918, filed Apr. 13, 2000.

BACKGROUND OF THE INVENTION

A large number of semiconductor gas sensors are presently in use in many parts of the world largely to provide early warning of the development of an explosion hazard (e.g. escaping flammable gas) or the presence of toxic gases or vapors in ambient air.

A sensing element normally comprising a semiconducting material and presenting a high surface-to-bulk ratio is deployed on a heated substrate between two metallic electrodes. The presence of gas posing a hazard is detected by a sensible change in the resistance of the semiconducting element by means of the electrodes that are incorporated in a suitable electric circuit. The device is thus a gas-sensitive resistor.

The most commonly used material in gas sensitive resistors used to measure impurity gases in air is tin dioxide. Tin dioxide sensors, though often useful in particular alarm functions, have generally been found to suffer from a lack of selectivity.

Semiconducting oxides for use in gas sensitive resistors must present surfaces of adequate extent capable of altering resistance in response to changes in the concentration of the target gas but not to changes in concentration of interferents such as relative humidity. The changes in resistance depend upon the oxide having an optimum electronic structure and a catalytic characteristic for interacting with the target gas.

A major objective in the development of S/C gas sensors is the avoidance of cross-sensitivity, initially from the ubiquitous interference from changes in the water vapor content of the atmosphere, since ambient RH levels vary freely in ambient atmospheres. There is also a need for selective response between different gases other than water vapor and the search for greater selectivity is now extending beyond tin oxide to other semi-conducting oxides.

The composition of the oxide surface dictates the way a semiconductor gas sensor performs.

If the particle size is 1 micron and the particles are equiaxed. Then a mono-layer surface coverage of a "foreign" oxide will represent an "impurity" concentration of 0.1 mole %. In fact, it has been reported that a surface covering of only one tenth of a mono-layer of silver oxide is sufficient to alter the sensing characteristics of tin oxide to more resemble those of silver oxide than of the substrate (tin oxide). (Ref. McAleer et al. 2,).

Following such considerations applicant's earlier patent, U.S. Pat. No. 5,811,662, describing the ozone detection characteristics of a $WO_3$ sensor teaches that the sensor material must be at least 99% pure.

Applicant's previous patent, U.S. Pat. No. 5,811,662, shows that tungsten trioxide, $WO_3$, is a useful sensor for ozone at low concentrations (1 ppm or less) in air but found that the $WO_3$ needed to be of 99% purity or better. Application, Ser. No. 09/132,216, shows that substoichiometric metal trioxides $MO_{3-x}$, where the metal is predominantly molybdenum, are useful in gas sensors for a number of gases. Further needs exist for superior detection of oxidizing gases, which is addressed by the present invention.

SUMMARY OF THE INVENTION

The present invention relates to sensors and more particularly to sensors suitable for use in gases and gaseous mixtures.

In a preferred embodiment, a sensor is provided that is suitable for use in a gas or gaseous mixture. The sensor includes a gas sensitive material capable of exhibiting a response in the form of an increase or a decrease in an electrical property of the material in the presence of a gas and that exhibits a small response to changes in the moisture content of the atmosphere.

In another preferred embodiment, the gas sensitive material is provided with two or more electrodes in communication with the gas sensitive material and the gas sensitive material is arranged so as to be capable of being contacted with a gas or gaseous mixture.

A sensor in accordance with the present invention may be used as a gas sensor in quantitative and/or qualitative determinations with gases or gaseous mixtures. The electrodes may be in direct communication with the gas sensitive material by being in contact therewith.

In this application, the term "gas" preferably embraces a gas as such and any material that may be present in a gaseous phase, one example of which is a vapor.

The gas sensitive material is a material which responds to a target gas without being affected by changes in relative humidity. Also, the term "gas sensitive material" means a preferred material which is gas (including vapor) sensitive in respect of an electrical property of the material.

The resistance and/or capacitance and/or impedance and/or conductance of the gas sensitive material depends upon the gas or gaseous mixture contacting the gas sensitive material. Thus, by measuring the resistance and/or capacitance and/or impedance of the gas sensitive material the composition of a gas or gaseous mixture can be sensed.

Since the resistance and/or capacitance and/or impedance and/or conductance of the gas sensitive material tends also to be temperature dependent, the sensor also preferably includes a temperature sensing means. The sensor may also include a heating means to enable operating temperature to be adjusted and/or contaminants to be burnt off if required.

It is to be understood that the sensitivity of a gas sensitive material may depend upon the composition of the gas sensitive material. Thus, by selection of the composition of the gas sensitive material its response to a particular gas may be optimized and its response to interferents, such as changes in relative humidity may be minimized.

The resistance and/or conductance and/or impedance may be measured directly. Alternatively, the measurement may be carried out indirectly by incorporating the sensor in a feedback circuit of an oscillator such that the oscillator frequency varies with composition of the gas or gaseous mixture. Gas composition may then be determined using an electronic counter. The signal thus produced may be used to modulate a radio signal and thereby be transmitted over a distance (e.g. by telemetry or as a pulse train along an optical fibre).

Examples of gases that respond to the present sensor include, but are not limited to, chlorine and ozone.

In one preferred embodiment of the present invention, the gas sensitive material has two or more electrodes in communication with said gas sensitive material, and the gas sensitive material and the electrodes are in contact with the same gas.

Preferably the gas sensitive material has porosity to give a satisfactory surface area for contact with the gas or gaseous mixture when in use.

The gas sensitive material, for example, may be prepared from an oxide or from an appropriate precursor. The oxide or precursor may optionally be prepared by a gel process such as a sol-gel process or a gel precipitation process.

The powder may be dried and calcined (e.g. for approximately 16 hours) at a temperature of about 700° C. depending upon the particular composition of gas sensitive material being prepared. The product resulting from calcination, which may be in the form of a cake, may be ground as required to give a fine powder. If required, grinding and calcination may be repeated several times in order to obtain a more suitable powder.

Subsequently, the fine powder may be pressed (e.g. with the optional addition of a binder, such as a solution of starch or polyvinyl alcohol) into any suitable shape (e.g. a pellet).

The pressing may be followed by a firing (e.g. at the same temperature as the calcination step(s) described above, or at a somewhat higher temperature, for approximately 16 hours).

In addition to assisting in the binding of the powder into desired shapes, the binder also burns out during the firing stage giving rise to porosity.

As an alternative a powder for subsequent calcination may be prepared, for example, by spray drying a solution (e.g. an aqueous solution) of appropriate starting material (e.g. a metal oxalate, metal acetate or metal nitrate).

Electrodes may be applied to the prepared gas sensitive material in any suitable manner. For example, electrodes (e.g. gold electrodes) may be applied by means of screen printing or sputtering.

Alternatively to preparing a sensor by forming a pellet and applying electrodes as disclosed above, a sensor in accordance with the present invention may be formed in any suitable manner. Thus, for example, a parallel plate configuration may be fabricated by applying a first electrode (e.g. of gold) to an insulating substrate (e.g. by screen printing or sputtering), forming a gas sensitive material layer covering at least a portion of the first electrode (e.g. by deposition, for example by screen printing or doctor blading from a suspension or a colloidal dispersion and firing at a temperature in the range of about 450°–700° C. to promote adhesion and mechanical integrity) and forming a second electrode (e.g. of gold) on the gas sensitive material layer (e.g. by screen printing or sputtering).

The second electrode is preferably permeable to facilitate access of gas or gaseous mixture in which the sensor is to be used to the gas sensitive material layer.

By way of further example, a coplanar configuration may be used in the preparation of a sensor in accordance with the present invention.

In such a coplanar configuration, interdigitated electrodes (e.g. of gold) may be formed on an insulating substrate (e.g. by screen printing or by sputtering or by photolithography and etching). The interdigitated electrodes are subsequently covered with a gas sensitive material layer (e.g. by means of deposition, for example by screen printing or doctor blading, from a suspension or a colloidal dispersion) and firing at a temperature in the range of about 450°–700° C. to promote adhesion and mechanical integrity.

The gas sensitive material disclosed by the present invention is comprised of a mixed oxides of general formula $W_xMo_{1-x}O_3$.

The inventor has now surprisingly found that the mixed oxide $W_xMo_{1-x}O_3$, where preferably x can be in the range 0.01 to 0.99, is very useful for the detection of oxidizing gases and in particular is superior for the detection of ozone. The preferred composition is in the range of 1% to 21% Mo (i.e. 99% to 79% W).

The present example in which the composition of the sensing material is in the range $W_xMo_{1-x}O_3$ with x varying from 0.01 to 0.99, is clearly distinct from the device claimed in applicant's earlier patent.

The inventor has also found that the precipitation of the material as a mixed oxide from an aqueous solution of the ammonium metallates in concentrations of the appropriate stoichiometric proportions yields a powder that can be screen-printed to give an ideal microstructure.

An added advantage of the mixed oxides is that the resistivity of the material may be tailored to a desired value by adjusting the Mo/W ratio within the single phase field. Varying this ratio can also adjust the catalytic properties of the material.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
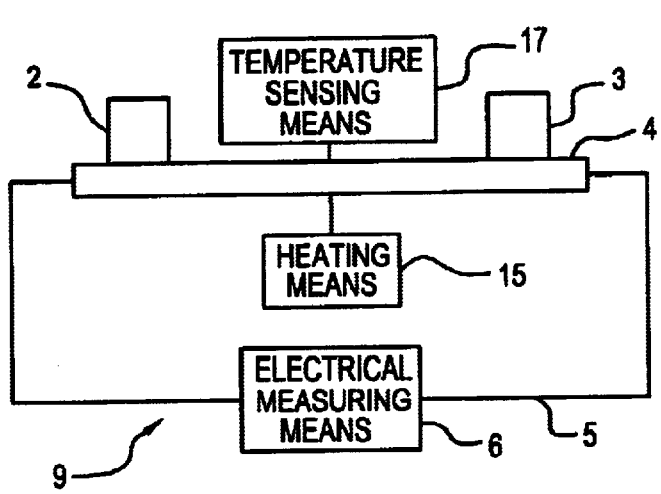
FIG. 1 is a diagrammatic representation of one form of a sensor in accordance with the present invention.

FIG. 1 shows a sensor 9 comprising a gas sensitive material 4 and, in contact with the gas sensitive material, gold electrodes 2 and 3. The gas sensitive material may be carried by a substrate (e.g. of alumina) (not shown).

Conductors 5 are provided to connect the electrodes 2 and 3 respectively to electrical measuring means 6 for measuring the resistance and/or capacitance and/or impedance of the gas sensitive material 4.

In operation a gas or gaseous mixture is contacted with the gas sensitive material 4.

The resistance and/or conductance and/or impedance is measured by the electrical measuring means 6. Changes in the composition of the gas or gaseous mixture which result in a change of resistance and/or conductance and/or capacitance and/or impedance are observed as changes in the resistance and/or conductance and/or capacitance and/or impedance recorded by the measuring means 6. Sensor 9 may include temperature sensing means 17 for sensing temperature and heating means for heating the sensor.

Figure 2:
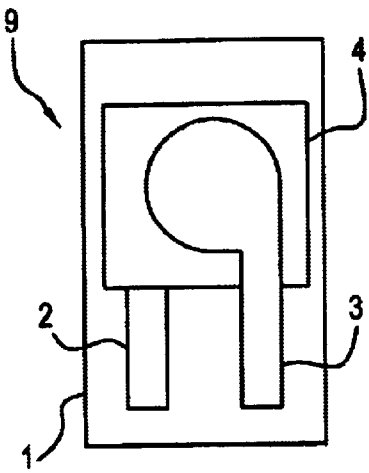
FIGS. 2 and 3 represent diagrammatically a parallel plate sensor in accordance with the present invention and a partially completed parallel plate sensor respectively.

FIG. 2 shows an insulating substrate 1 (e.g. an alumina ceramic tile) upon which is formed a first electrode 2 (e.g. of gold), a gas sensitive material layer 4 comprising a gas sensitive material in accordance with the present invention and a second electrode 3 (e.g. of gold).

A parallel plate sensor 9, as shown in FIG. 2, may be fabricated by applying the first electrode 2 (e.g. of gold) to the insulating substrate 1 (e.g. by screen printing or sputtering), forming a gas sensitive material layer 4 by deposition, for example by screen printing or doctor blading, from a suspension or a colloidal dispersion and firing at a temperature in the range 450°–700° C. to promote adhesion and mechanical integrity and forming a second electrode 3 (e.g. of gold) on the gas sensitive material layer 4, (e.g. by screen printing or sputtering).

Figure 3:
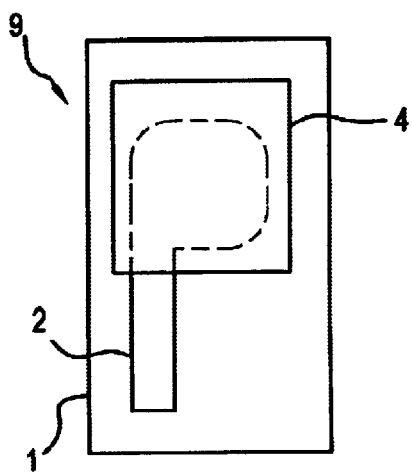

In order to facilitate understanding of the construction of the sensor of FIG. 2 reference may be made to FIG. 3, which shows a parallel plate sensor 9 of the type shown in FIG. 2 partially completed inasmuch as the second electrode 3 has not been formed. FIG. 3 thus shows the insulating substrate 1, the first electrode 2 and the gas sensitive material layer 4 and it is seen that the portion of the first electrode 2 covered by the gas sensitive material layer 4 may preferably extend in area to substantially the same extent as the second electrode 3.

In operation, the first electrode 2 and second electrode 3 are connected to an electrical measuring means (not shown) for measuring the resistance and/or capacitance and/or impedance of the gas sensitive material layer 4 and the sensor is contacted with a gas or gaseous mixture. The resistance and/or capacitance and/or impedance is measured by the electrical measuring means and changes in the composition of the gas or gaseous mixture which result in a change of resistance and/or capacitance and/or impedance are observed as changes in the resistance and/or capacitance and/or impedance recorded by the electrical measuring means.

Figure 4:
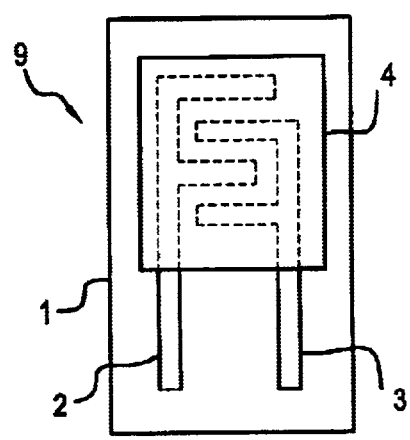
FIG. 4 is a diagrammatic representation of a coplanar sensor in accordance with the present invention.

FIG. 4 shows an insulating substrate 1 (e.g. an alumina ceramic tile) upon which are formed electrodes 2 and 3 (e.g. both of gold), and a gas sensitive material layer 4 comprising a gas sensitive material in accordance with the present invention. It is seen from the lines shown in dotted form in FIG. 4 that the portions of the first electrode 2 and second electrode 3 covered by the gas sensitive material layer 4 are interdigitated.

The first electrode 2 and the second electrode 3 may be provided on the insulating substrate 1 by any suitable method. For example, the methods disclosed for providing electrodes 2 and 3 in the parallel plate sensor, described with reference to FIG. 2 and FIG. 3, may be used.

The gas sensitive material layer 4 shown in FIG. 4 may be prepared by any suitable method. For example, the methods disclosed for preparing gas sensitive material layer 4 in FIG. 2 and FIG. 3 may be used.

A series of mixed oxides $W_xMo_{1-x}O_3$, where preferably x can be in the range 0.01 to 0.99, is very useful for the detection of oxidizing gases and in particular is superior for the detection of ozone. The preferred composition is in the range of 1% to 21% Mo (i.e. 99% to 79% W).

The precipitation of the material as a mixed oxide from an aqueous solution of the ammonium metallates in concentrations of the appropriate stoichiometric proportions yields a powder that can be screen-printed to give an ideal microstructure.

An added advantage of the mixed oxides is that the resistivity of the material may be tailored to a desired value by adjusting the Mo/W ratio within the single phase field. Varying this ratio can also adjust the catalytic properties of the material.

EXAMPLES

Example 1

48 grams of $(NH_4)_6W_7O_{24}.6H_2O$ and 5 grams of $(NH_4)_6Mo_7O_{24}.4H_2O$ were dispersed in 500 mls of distilled water in a teflon coated boiler. The mixed solution was evaporated to dryness over a period of 3 hours. It is also possible to precipitate the mixed oxide by adding an excess of ethanol. The dried powder was heated in a closed furnace to 700° C. for 2 hours. The powder was dispersed in an organic vehicle and screen printed over gold interdigitated electrodes on an alumina substrate to give an oxide layer thickness of 50 microns.

Figure 5:
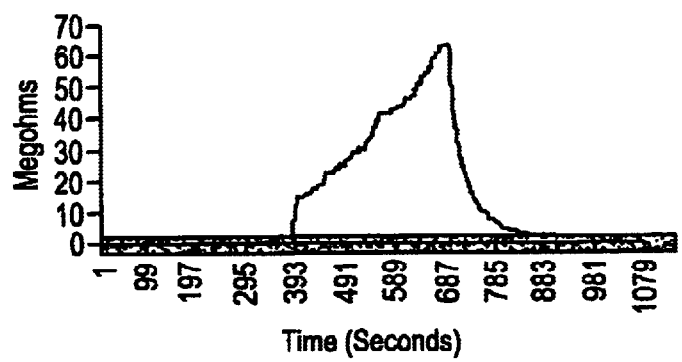
FIG. 5 is a graph of response of a $W_xMo_{1-x}O_3$ sensor to a pulse of 100 parts per billion of ozone in dry air.

The tiles, which had previously been equipped with a platinum resistance heater printed on the reverse, were fired at 700° C. for ½ hour. Supplying the heater with current from two dry cells (3.2 volts, ~1 Watt) raised the sensor to the operating temperature so that the resistance of the oxide layer became very sensitive to the presence of ozone as shown in FIG. 5 which shows the response to a pulse of 100 parts per billion of ozone in a background of dry air.

The response of the sensor to changes in relative humidity (RH) was very small, no more than a drop in resistance of 12 kohms for an increase in RH from 48% to 96%.

Gases that the sensor may detect include, but are not limited to, chlorine and ozone.

Figure 6:
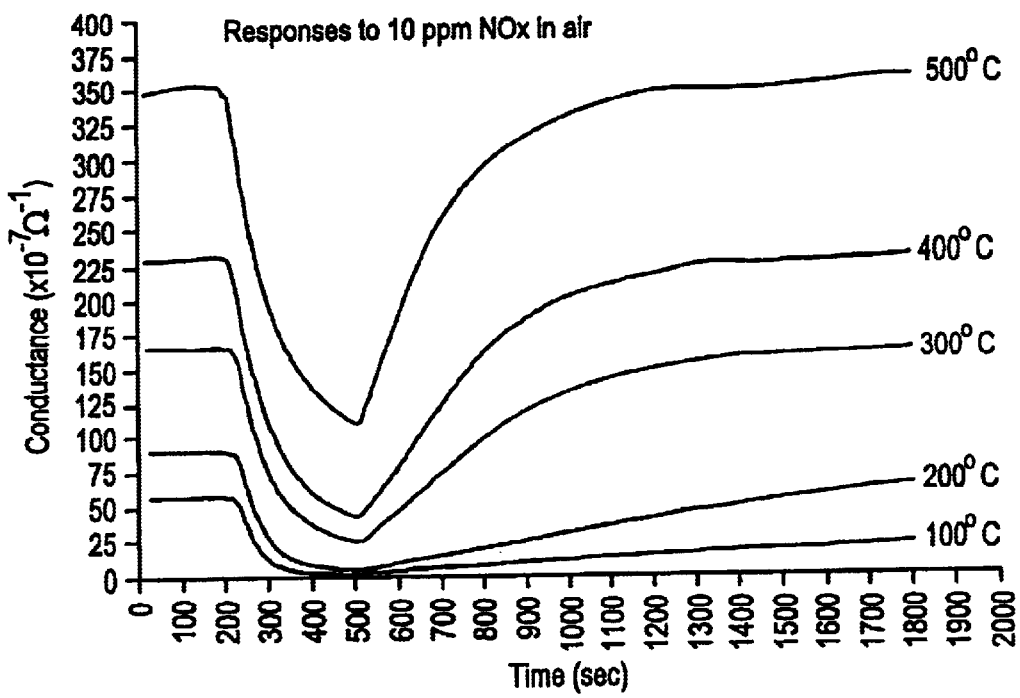
FIG. 6 shows responses to 10 ppm $NO_x$ in air.

Further examples of the behavior of samples similar to that in example 1 are that the sensor has a good response to the presence of NO2 (another oxidizing gas) in air as shown in FIG. 6.

Figure 7:
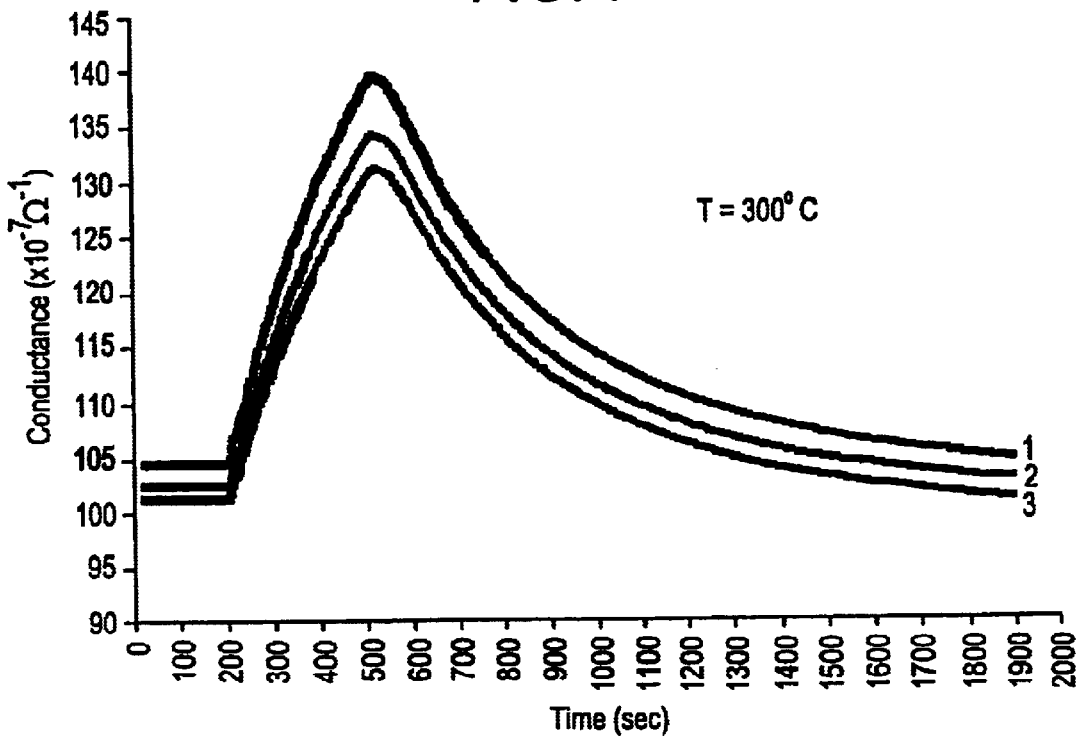
FIG. 7 shows changes in conductance brought about by changes in relative humidity in the air from dry air to water saturated air at 300° C.

At the same time the sensor suffers from only a small potential interference from changes in relative humidity. FIG. 7 shows the change in conductance brought about by a maximum change in RH (i.e. from dry air to water-saturated air) at 300° C. This is a very much smaller response to water vapor than is shown for tin oxide. At the same temperature tin oxide exhibits a change in conductance of over one order of magnitude, in response to this type of change in RH.

It should also be noted that the activation energy for conduction for these sensors is very small—around 0.1 eV—so that the sensitivity to changes in operating temperature is very much smaller than is the case for sensors employing tin dioxide.

A further advantage of these sensors is that, at low temperatures (100°–250° C.) the conductance response depends on the square of the NO2 concentration. This unusual response pattern is useful in providing an enhanced signal at concentrations of the gas that are in the range which is a threat to human health.

While the invention has been described with reference to specific embodiments, modifications and variations of the invention may be constructed without departing from the scope of the invention, which is defined in the following claims.

I claim:

1. An oxidizing gas sensor comprising a sensor material of mixed oxide $W_xMo_{1-x}O_3$, where x is in the range 0.01 to 0.99 for detecting oxidizing gases, particularly ozone, where the preferred composition is in the range of 1 mole % to 21 mole % Mo (99 mole % to 79 mole % W).

2. A method of preparation of the sensor material of claim 1 comprising precipitating the material as a mixed oxide from an aqueous solution of the ammonium metallates in concentrations of stoichiometric proportions, yielding a powder, screen-printing the powder on a substrate to give a microstructure.

3. The sensor of claim 1, further comprising first and second electrodes spaced apart by the sensor material which is gas sensitive, which contacts both the first and second electrodes.

4. A method of sensing concentrations of oxidizing gases, particularly ozone, $NO_x$ and chlorine in other gases, comprising contacting the sensor material as described in claim 3, with a gas suspected of having a partial pressure of ozone, $NO_x$ or chlorine, and sensing change in conductance, resistance, capacitance and/or impedance in an electrical circuit including the oxidizing gas sensitive sensor material between the first and second electrodes.

5. The method of claim 4, further comprising imposing a potential between the first and second electrodes and sensing changes in an electrical circuit between the first and second electrodes.

6. The method of claim 5, further comprising imposing a potential of about 0.1 eV between the first and second electrodes.

7. A method of measuring concentrations of oxidizing gases, particularly ozone, chlorine and $NO_x$ in other gases, comprising contacting the sensor material as described in claim 3, with a gas suspected of having a partial pressure of ozone, chlorine or $NO_x$, and measuring change in conductance, resistance, capacitance and/or impedance in the gas sensitive sensor material between the first and second electrodes.

8. The method of claim 7, further comprising imposing a potential between the first and second electrodes and measuring changes in an electrical circuit between the first and second electrodes.

9. The method of claim 8, further comprising imposing a potential of about 0.1 eV between the first and second electrodes.

10. The method of claim 7, further comprising depositing the first and second electrodes spaced apart on a substrate, placing the sensor material on the substrate, heating the substrate, sensing temperature of the substrate and measuring conductance, impedance, capacitance or resistance between the electrodes.

11. An oxidizing gas sensor, comprising a first electrode, a gas sensitive sensor material in contact with the first electrode, a second electrode in contact with the gas sensitive sensor material and spaced from the first electrode, wherein the gas sensitive sensor material is $W_xMo_{1-x}O_3$.

12. The sensor of claim 10, wherein the x is not less than 0.01.

13. The sensor of claim 10, wherein the x is not greater than 0.99.

14. The sensor of claim 10, wherein the Mo is present in a concentration not less than 1 mole % with respect to a combined amount of W and Mo.

15. The sensor of claim 10, wherein the Mo is present in a concentration not less than 2 mole % with respect to a combined amount of W and Mo.

16. The sensor of claim 10, wherein the W is present in a concentration not less than 79 mole % with respect to a combined amount of W and Mo.

17. The sensor of claim 10, wherein the W is present in a concentration not less than 99 mole % with respect to a combined amount of W and Mo.

18. The sensor of claim 1, further comprising a substrate, at least one of the electrodes being disposed on the substrate, a heater connected to the substrate for heating the substrate and the gas sensitive sensor material, a circuit connected to the electrodes, a source of electrical potential connected to the electrodes, and a conductance, resistance, capacitance or impedance sensor connected to the circuit.

* * * * *